United States Patent
Guthrie et al.

(10) Patent No.: US 9,728,818 B2
(45) Date of Patent: Aug. 8, 2017

(54) BATTERY STATUS DETECTION AND STORAGE METHOD AND SYSTEM IN MEDICAL MONITORING

(71) Applicant: LifeScan Scotland Limited, Inverness (GB)

(72) Inventors: Brian Guthrie, Inverness (GB); Allan Macrae, Inverness (GB)

(73) Assignee: LifeScan Scotland Limited, Inverness (GB)

(*) Notice: Subject to any disclaimer, the term of this patent is extended or adjusted under 35 U.S.C. 154(b) by 186 days.

(21) Appl. No.: 14/388,316

(22) PCT Filed: Mar. 27, 2013

(86) PCT No.: PCT/GB2013/050796
§ 371 (c)(1),
(2) Date: Sep. 26, 2014

(87) PCT Pub. No.: WO2013/144617
PCT Pub. Date: Oct. 3, 2013

(65) Prior Publication Data
US 2015/0048836 A1    Feb. 19, 2015

Related U.S. Application Data

(60) Provisional application No. 61/618,601, filed on Mar. 30, 2012.

(51) Int. Cl.
*H01M 10/42* (2006.01)
*A61B 5/145* (2006.01)
(Continued)

(52) U.S. Cl.
CPC ....... *H01M 10/425* (2013.01); *A61B 5/14532* (2013.01); *G01R 31/362* (2013.01);
(Continued)

(58) Field of Classification Search
CPC .................................................. G01R 31/362
(Continued)

(56) References Cited

U.S. PATENT DOCUMENTS 5,032,825 A * 7/1991 Kuznicki ............. G08B 21/185
                                                        320/136
6,150,823 A * 11/2000 Takahashi .......... G01R 31/3631
                                                        324/427
(Continued)

FOREIGN PATENT DOCUMENTS

CN    101052889 A    10/2007
CN    101772322 A     7/2010
(Continued)

OTHER PUBLICATIONS

Search Report issued in corresponding Chinese Patent Application No. 201380018107.2, dated Feb. 4, 2016, 3 pages.
(Continued)

*Primary Examiner* — Samuel Berhanu
*Assistant Examiner* — Tessema Kebede

(57) ABSTRACT

Described herein are systems and methods to determine when a new or fresh battery has been replaced in a medical monitoring device and store a record of such battery replacement so that the battery records of the medical monitoring device can be reliably kept over the life of the monitoring device.

25 Claims, 3 Drawing Sheets

(51) Int. Cl.
*H01M 6/50* (2006.01)
*H01M 10/48* (2006.01)
*G01R 31/36* (2006.01)

(52) U.S. Cl.
CPC ..... *H01M 6/5083* (2013.01); *H01M 10/4285* (2013.01); *H01M 10/48* (2013.01); *A61B 2560/0214* (2013.01); *A61B 2560/0431* (2013.01); *G01R 31/36* (2013.01); *H01M 10/42* (2013.01); *H01M 2220/30* (2013.01)

(58) Field of Classification Search
USPC ........................................................ 324/427
See application file for complete search history.

(56) References Cited

U.S. PATENT DOCUMENTS

| | | | |
|---|---|---|---|
| 6,169,387 B1* | 1/2001 | Kaib | A61N 1/3931 320/132 |
| 6,179,979 B1 | 1/2001 | Hodges et al. | |
| 6,191,557 B1 | 2/2001 | Gray et al. | |
| 6,193,873 B1 | 2/2001 | Ohara et al. | |
| 6,284,125 B1 | 9/2001 | Hodges et al. | |
| 6,304,088 B1 | 10/2001 | Yee | |
| 6,413,410 B1 | 7/2002 | Hodges et al. | |
| 6,475,372 B1 | 11/2002 | Ohara et al. | |
| 6,549,014 B1 | 4/2003 | Kutkut et al. | |
| 6,716,577 B1 | 4/2004 | Yu et al. | |
| 6,749,887 B1 | 6/2004 | Dick et al. | |
| 6,863,801 B2 | 3/2005 | Hodges et al. | |
| 6,890,421 B2 | 5/2005 | Ohara et al. | |
| 7,045,046 B2 | 5/2006 | Chambers et al. | |
| 7,194,308 B2* | 3/2007 | Krig | A61N 1/3708 324/433 |
| 7,291,256 B2 | 11/2007 | Teodorczyk et al. | |
| 7,498,132 B2 | 3/2009 | Yu et al. | |
| 7,737,581 B2* | 6/2010 | Spurlin | A61M 5/1723 307/66 |
| 7,907,060 B2 | 3/2011 | Reams | |
| 8,009,054 B2* | 8/2011 | Reams | G01R 31/362 324/426 |
| 8,071,028 B2* | 12/2011 | Andrews | C12Q 1/54 422/50 |
| 2002/0058906 A1* | 5/2002 | Lebel | A61M 5/172 604/65 |
| 2005/0009126 A1* | 1/2005 | Andrews | C12Q 1/54 435/14 |
| 2005/0084754 A1 | 4/2005 | Klein | |
| 2005/0102005 A1 | 5/2005 | Krig et al. | |
| 2007/0040449 A1 | 2/2007 | Spurlin et al. | |
| 2007/0159321 A1 | 7/2007 | Ogata et al. | |
| 2008/0312852 A1* | 12/2008 | Maack | A61N 1/3708 702/63 |
| 2009/0278701 A1* | 11/2009 | Reams | G01R 31/362 340/636.15 |
| 2010/0331654 A1* | 12/2010 | Jerdonek | A61B 5/14532 600/365 |
| 2011/0054282 A1 | 3/2011 | Nekoomaram et al. | |
| 2011/0098600 A1 | 4/2011 | Matsumura et al. | |

FOREIGN PATENT DOCUMENTS

| | | |
|---|---|---|
| CN | 102195304 A | 9/2011 |
| JP | 2001185238 A | 7/2001 |
| JP | 2001245857 A | 9/2001 |
| JP | 2004230152 A | 8/2004 |
| JP | 2007184754 A | 7/2007 |
| RU | 2364012 C2 | 8/2009 |

OTHER PUBLICATIONS

First Office Action issued in corresponding Chinese Patent Application No. 201380018107.2, dated Feb. 19, 2016, 34 pages.
International Preliminary Report on Patentability issued in related International Patent Application No. PCT/GB2013/050796, dated Oct. 1, 2014, 9 pages.
"Low-Power, Single/Dual-Level Battery Monitors with Hysteresis", Dec. 1, 2005, XP055069284, Retrieved from the Internet: URL: www.maxim-ic.com [retrieved on Mar. 15, 2013] the whole document.
International Search Report and Written Opinion issued in related International Application No. PCT/GB2013/050796, mailed Jul. 17, 2013, 13 pages.
Search Report issued in related Taiwan Patent Application No. 102111309, dated Jul. 22, 2016, 21 pages. (With partial English translation.).
Second Office Action issued in related Chinese Patent Application No. 201380018107.2, dated Oct. 26, 2016, 25 pages.
Patent Examination Report No. 1 issued in related Australian Patent Application No. 2013239446, dated Oct. 27, 2016, 3 pages.
Notice of Reasons for Rejection issued in corresponding Japanese Patent Application No. 2015-502449, dated Feb. 19, 2017, 5 pages.
Official Action issued in corresponding Russian Patent Application No. 2014143774, dated May 18, 2017, 17 pages.
Notice of Reasons for Rejection issued in corresponding Japanese Patent Application No. 2015-502449, dated Feb. 19, 2017, 5 pages. (Previously Submitted on May 18, 2017; Fee Paid Jun. 28, 2017).

* cited by examiner

BATTERY STATUS DETECTION AND STORAGE METHOD AND SYSTEM IN MEDICAL MONITORING

PRIORITY

This application is the National Stage under Section 371 of International Patent Application PCT/GB2013/050796 filed on Mar. 27, 2013, which application claims the benefits of priority of prior filed U.S. Provisional Patent Application Ser. No. 61/618,601 filed on Mar. 30, 2012, which prior applications are hereby incorporated by reference as if fully set forth herein.

BACKGROUND

Biosensors such as glucose sensor (strip type and continuous monitoring type), electrocardiogram, blood pressure, and the like use batteries in its controllers or monitors. The batteries can be in the form of rechargeable or disposable batteries. The batteries are usually monitored to ensure that there is sufficient power to complete many of the tasks assigned to the sensors. For diagnostic purposes, the batteries' state or charge or other operating parameters can be periodically recorded with the biosensor measurement results and stored in static or non-volatile memory so that performance of the device or the battery can be tracked over the lifetime of the device. However, the non-volatile memory may have only a limited amount of storage allocated to both measurement results and device diagnostic data. In the event that the device runs out of memory, the oldest memory is deleted, which deleted memory may include the battery records.

SUMMARY OF THE DISCLOSURE

Applicant has devised a portable medical measurement system that has a battery operational for twice the number of storage cells allotted for measurements and diagnostic data. For example, in applicant's system, the number of measurement tests that can be stored is about 1000 measurement tests before the oldest stored measurement is deleted and replaced with the newest measurement. The battery for this system, however, is operational for at least 2000 measurements. This means that the data regarding the battery may not be stored because of the deletion of the oldest memory, which may include battery change information. Consequently, applicant has recognized that in portable medical measurement systems, a need exist to determine when a battery of the system has changed or fully charged in order to permit quality control and post-launch product analysis. Because this battery change information may be lost due to the longer operational state of the battery as compared to memory storage allocated, applicant has recognized a need to store this battery change information separate from the battery diagnostic. However, when a sensing switch is used in conjunction with the battery to detect battery removal, applicant has discovered that this type of sensing switch can be fooled by a removing the battery and re-inserting the battery. To implement a battery change record that is reliable and trustworthy, applicant has devised a technique to detect a battery change or even a change of a rechargeable battery without using a sensing switch and its attendant problem of false positive detection.

In one aspect, a method of monitoring power in a portable physiological measurement device that has at least a battery coupled to a processor and memory. The method can be achieved by: turning on the device; Measuring power of the battery; Determining if the power level of the battery is greater than a first threshold; If the power level is less than or equal to the first threshold then setting a flag for low battery as true otherwise performing start up checking process of the device; after the performing of the startup checking process, evaluating the battery to determine if both the power level of the battery is greater than a second threshold and the low battery flag is set as true; if the evaluating step is affirmative then recording the time and date of the evaluating step to memory and setting the flag for low battery as false and annunciating a status of the battery in the device; if the evaluating step is negative, then conducting an analyte measurement; checking the power level of the battery against the first threshold; if the checking indicates that power level is greater than the first threshold then annunciating a result of the physiological measurement otherwise ending the checking step.

In another aspect, a method of monitoring battery power in a portable electronic medical device is provided. The device has at least a battery coupled to a processor and memory. The method can be achieved by: measuring a power level of the battery; determining if the power level of the battery is greater than a first threshold; if the power level is less than or equal to the first threshold then setting a flag for low battery as true otherwise performing other process step for the device; after the performing of other process step, evaluating the battery to determine if both the power level of the battery is greater than a second threshold and the low battery flag is set as true; if the evaluating step is affirmative then recording the time and date of the evaluating step to memory and setting the flag for low battery as false; and annunciating a change in status of the battery in the device.

In these aspects described above, the conducting of the physiological measurement may also include measuring an amount of analyte in a biosensor unit; in which the battery includes two Alkaline AA-sized batteries, and the first threshold may be about 2.5 volts for the battery; alternatively, the first threshold may be about 82% of the rated voltage or amperage of the battery; the second threshold may be about 96% of the rated voltage or amperage of the battery; alternatively, the second threshold may be about 2.9 volts for the battery.

Furthermore, in these aspects described above, the performing may further include providing a tutorial for operation of the device; the annunciating may include displaying the time and date of the evaluating to indicate that the battery has been recharged or changed; or may further include terminating operation of the method whenever the power level of the battery is below the first threshold; the annunciating may include displaying the time and date of the evaluating to indicate that the battery has been recharged or changed; or the method may further include terminating operation of the method whenever the power level of the battery is below the first threshold.

In yet a further aspect, a physiological measurement system is provided that includes a biosensor unit and a portable disease management unit. The biosensor unit provides physiological data of a user while the portable disease management unit includes a microprocessor. The microprocessor is in communication with the biosensor unit to receive a plurality of physiological measurements reflective of a health condition of the user. The microprocessor is also coupled to a memory and a battery and configured to: set a low battery flag as true when a power level of the battery is lower than a first threshold; evaluate whether both a power level of the battery is greater than a second threshold and the low battery flag is true; store in the memory a time and date when an evaluation is affirmative for both the power level of the battery is greater than a second threshold and the low battery flag is true; set the low battery flag as false when the time and date of the evaluation is stored in memory; and annunciate that a status of the battery has changed at the time and date stored in memory.

In these aspects describe above, the microprocessor is configured, upon being turned on, to: measure a power of the battery; determine if the power level of the battery is greater than the first threshold; if the power level is determined to be greater than the first threshold then perform start up process of the device; measure analyte with the biosensor unit; check the power level of the battery against the first threshold; and annunciate a result of the physiological measurement if the power level is greater than the first threshold otherwise terminate operation.

Moreover, the physiological measurement includes measurement of an amount of analyte from a physiological fluid in the biosensor unit in the form of a test strip; in which the battery includes two Alkaline AA-sized batteries, and the first threshold may be about 2.5 volts for the battery; alternatively, the first threshold may be about 82% of the rated voltage or amperage of the battery; the second threshold may be about 96% of the rated voltage or amperage of the battery; alternatively, the second threshold may be about 2.9 volts for the battery; the start up process further comprises display of a tutorial for operation of the device; the annunciate comprises display of the time and date of the evaluation to indicate that the battery has been recharged or changed.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE FIGURES

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject invention in a human patient represents a preferred embodiment.

Figure 1A:
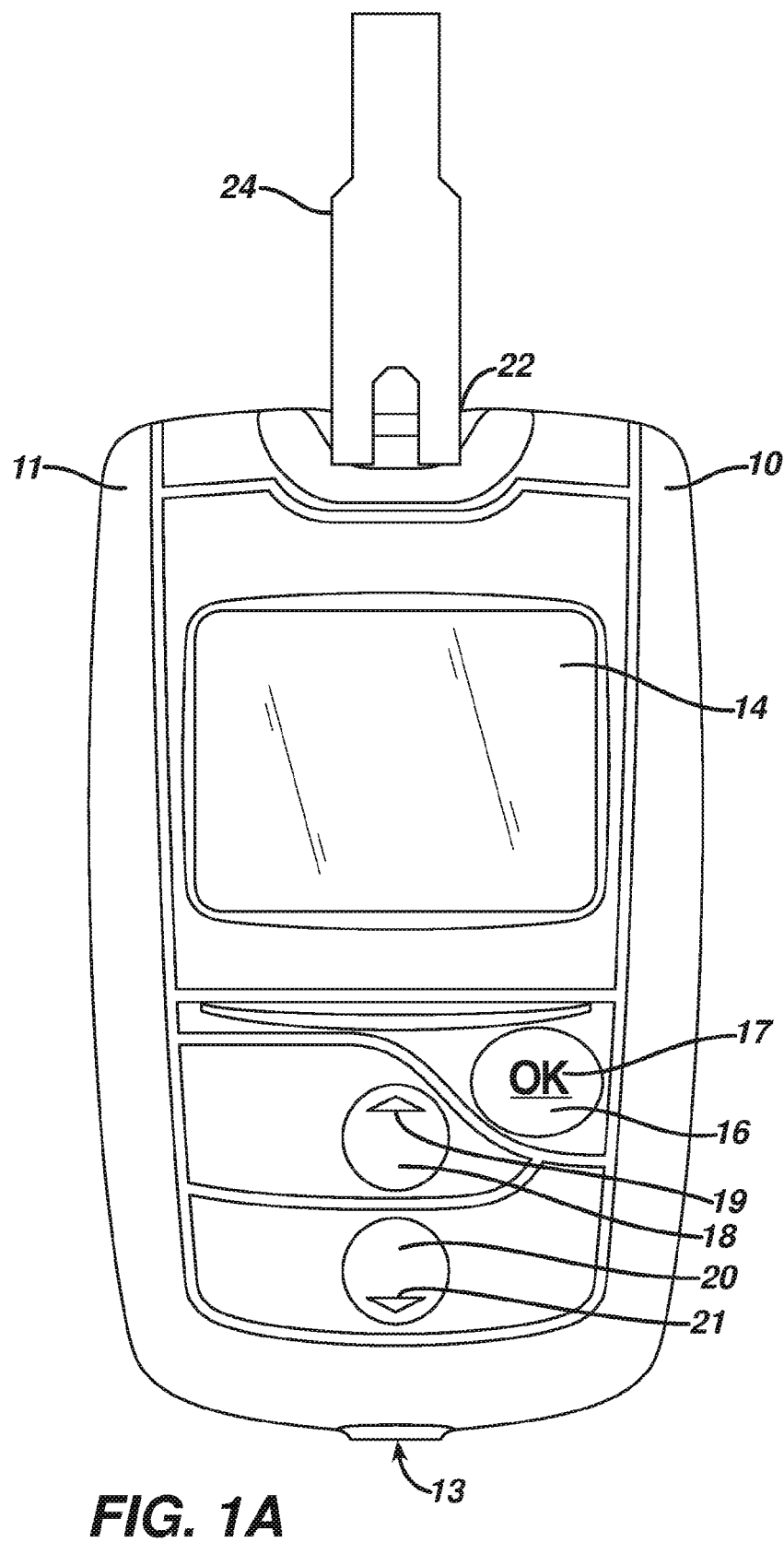
FIG. 1A illustrates a chronic disease management system that includes a physiological measurement and data management unit and a biosensor.

FIG. 1A illustrates a chronic disease management system that includes a data management unit 10 ("DMU") and a biosensor in the form of a physiological measurement test strip 24. It is noted that while the biosensor is shown in the form of a test strip to test blood glucose, a continuous glucose monitor can also be utilized as an alternative to the embodiments described herein to provide for physiological data in the form of glucose measurements in physiological fluids.

Analyte meter or DMU 10 can include a housing 11, user interface buttons (16, 18, and 20), a display 14, a strip port connector 22, and a data port 13, as illustrated in FIG. 1A. User interface buttons (16, 18, and 20) can be configured to allow the entry of data, navigation of menus, and execution of commands. Data can include values representative of analyte concentration, and/or information, which are related to the everyday lifestyle of an individual. Information, which is related to the everyday lifestyle, can include food intake, medication use, occurrence of health check-ups, and general health condition and exercise levels of an individual. Specifically, user interface buttons (16, 18, and 20) include a first user interface button 16, a second user interface button 18, and a third user interface button 20. User interface buttons (16, 18, and 20) include a first marking 17, a second marking 19, and a third marking 21, respectively, which allow a user to navigate through the user interface. Although the buttons are shown as mechanical switches, a touch screen interface with virtual buttons may also be utilized. As represented in FIG. 1A, the DMU is provided with various user-interfaces including the user interface UI to provide for consistency or progressivity feedback to the user's analyte measurements over time.

Figure 1B:
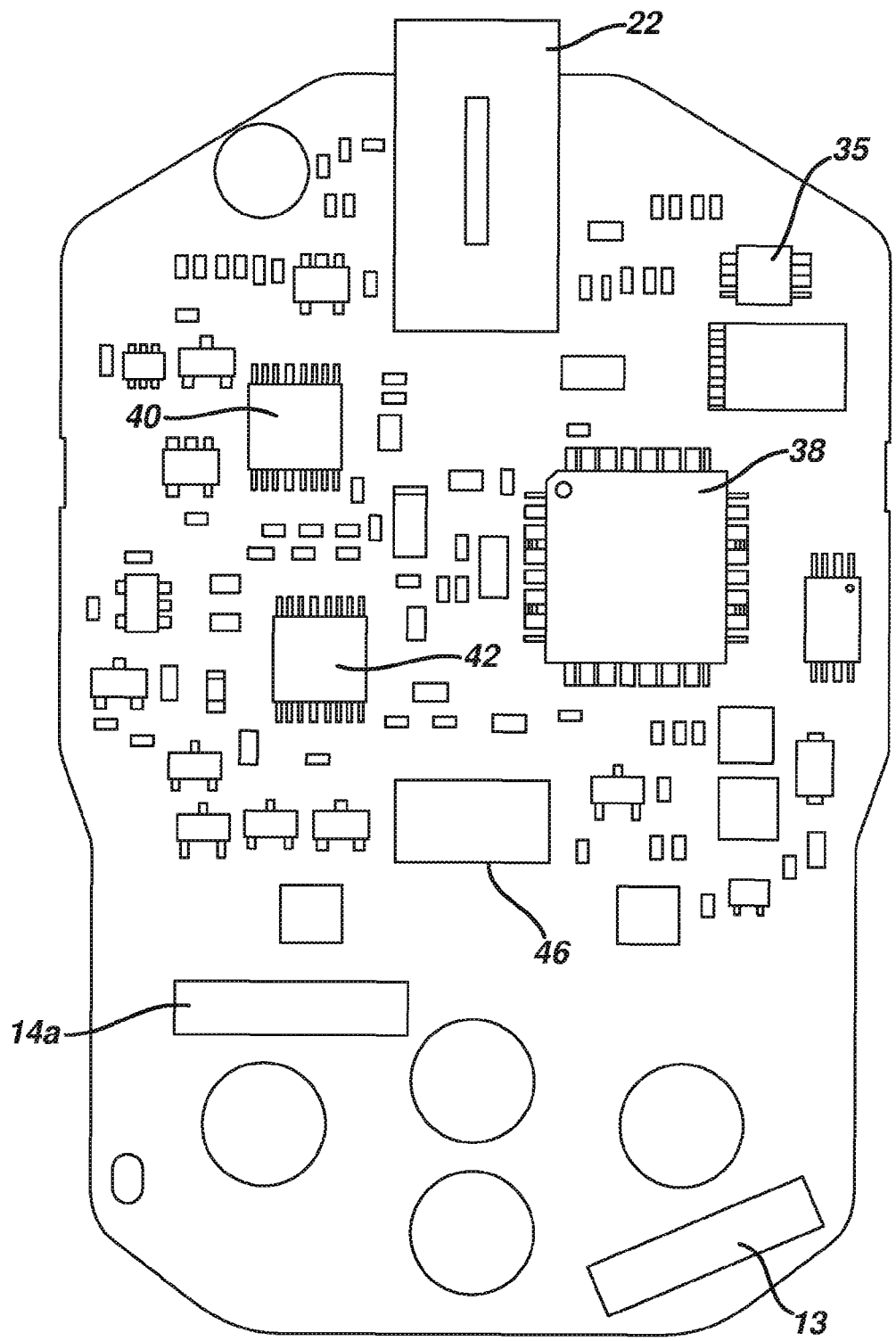
FIG. 1B illustrates, in simplified schematic, an exemplary circuit board of a chronic disease data management unit.

The electronic components of meter 10 can be disposed on a circuit board 34 that is within housing 11. FIG. 1B illustrates (in simplified schematic form) the electronic components disposed on a top surface of circuit board 34. On the top surface, the electronic components include a strip port connector 22, an operational amplifier circuit 35, a microcontroller 38, a display connector 14a, a non-volatile memory 40, a clock 42, and a first wireless module 46. On the bottom surface, the electronic components may include a battery connector (not shown) and a data port 13. Microcontroller 38 can be electrically connected to strip port connector 22, operational amplifier circuit 35, first wireless module 46, display 14, non-volatile memory 40, clock 42, battery, data port 13, and user interface buttons (16, 18, and 20).

Operational amplifier circuit 35 can include two or more operational amplifiers configured to provide a portion of the potentiostat function and the current measurement function. The potentiostat function can refer to the application of a test voltage between at least two electrodes of a test strip. The current function can refer to the measurement of a test current resulting from the applied test voltage. The current measurement may be performed with a current-to-voltage converter. Microcontroller 38 can be in the form of a mixed signal microprocessor (MSP) such as, for example, the Texas Instrument MSP 430. The TI-MSP 430 can be configured to also perform a portion of the potentiostat function and the current measurement function. In addition, the MSP 430 can also include volatile and non-volatile memory. In another embodiment, many of the electronic components can be integrated with the microcontroller in the form of an application specific integrated circuit (ASIC).

Strip port connector 22 can be configured to form an electrical connection to the test strip. Display connector 14a can be configured to attach to display 14. Display 14 can be in the form of a liquid crystal display for reporting measured analyte levels, and for facilitating entry of lifestyle related information. Display 14 can optionally include a backlight. Data port 13 can accept a suitable connector attached to a connecting lead, thereby allowing glucose meter 10 to be linked to an external device such as a personal computer. Data port 13 can be any port that allows for transmission of data such as, for example, a serial, USB, or a parallel port. Clock 42 can be configured to keep current time related to the geographic region in which the user is located and also for measuring time. The DMU can be configured to be electrically connected to a power supply such as, for example, a battery.

Referring back to FIG. 1A, analyte test strip 24 can be in the form of an electrochemical physiological measurement test strip. Test strip 24 can include one or more working electrodes and a counter electrode. Test strip 24 can also include a plurality of electrical contact pads, where each electrode can be in electrical communication with at least one electrical contact pad. Strip port connector 22 can be configured to electrically interface to the electrical contact pads and form electrical communication with the electrodes. Test strip 24 can include a reagent layer that is disposed over at least one electrode. The reagent layer can include an enzyme and a mediator. Exemplary enzymes suitable for use in the reagent layer include glucose oxidase, glucose dehydrogenase (with pyrroloquinoline quinone co-factor, "PQQ"), and glucose dehydrogenase (with flavin adenine dinucleotide co-factor, "FAD"). An exemplary mediator suitable for use in the reagent layer includes ferricyanide, which in this case is in the oxidized form. The reagent layer can be configured to physically transform glucose into an enzymatic by-product and in the process generate an amount of reduced mediator (e.g., ferrocyanide) that is proportional to the glucose concentration. The working electrode can then measure a concentration of the reduced mediator in the form of a current. In turn, glucose meter 10 can convert the current magnitude into a glucose concentration. Details of the preferred test strip are provided in U.S. Pat. Nos. 6,179,979; 6,193,873; 6,284,125; 6,413,410; 6,475,372; 6,716,577; 6,749,887; 6,863,801; 6,890,421; 7,045,046; 7,291,256; 7,498,132, all of which are incorporated by reference in their entireties herein.

When a user takes a physiological measurement (e.g., a blood physiological measurement test) with the meter 10, the meter 10 measures the battery voltage to determine whether there is enough power left to complete the test and safely store the result in memory. As part of product analysis or quality control, the meter is configured to record the battery voltage along with the test result to and additional test details (e.g., time and date, glucose level, meal tag index, test counter etc.) as part of a data record structure. However, it is noted that while the meter 10 is configured to store a fixed number of test records, fresh batteries for the meter will last over 2000 tests. When the test memory is full the oldest result drops off allowing the latest result to be saved. Relying on the enhanced glucose records alone to see when or if a user has changed a battery could be lost, let alone seeing how many times in the life of the meter the batteries have been changed. Therefore the meter 10 is provided with new memory record type called the Battery Change Record distinct from the data record structure so that battery changes or charges may be stored without being lost due to the deletion of the oldest records when memory storage is exceeded. To determine if a battery is changed without the need of an additional sensing switch circuitry, which also be falsely triggered by a user removing and reinserting the old batteries, a process has been developed as referenced exemplarily in FIG. 2.

Figure 2:
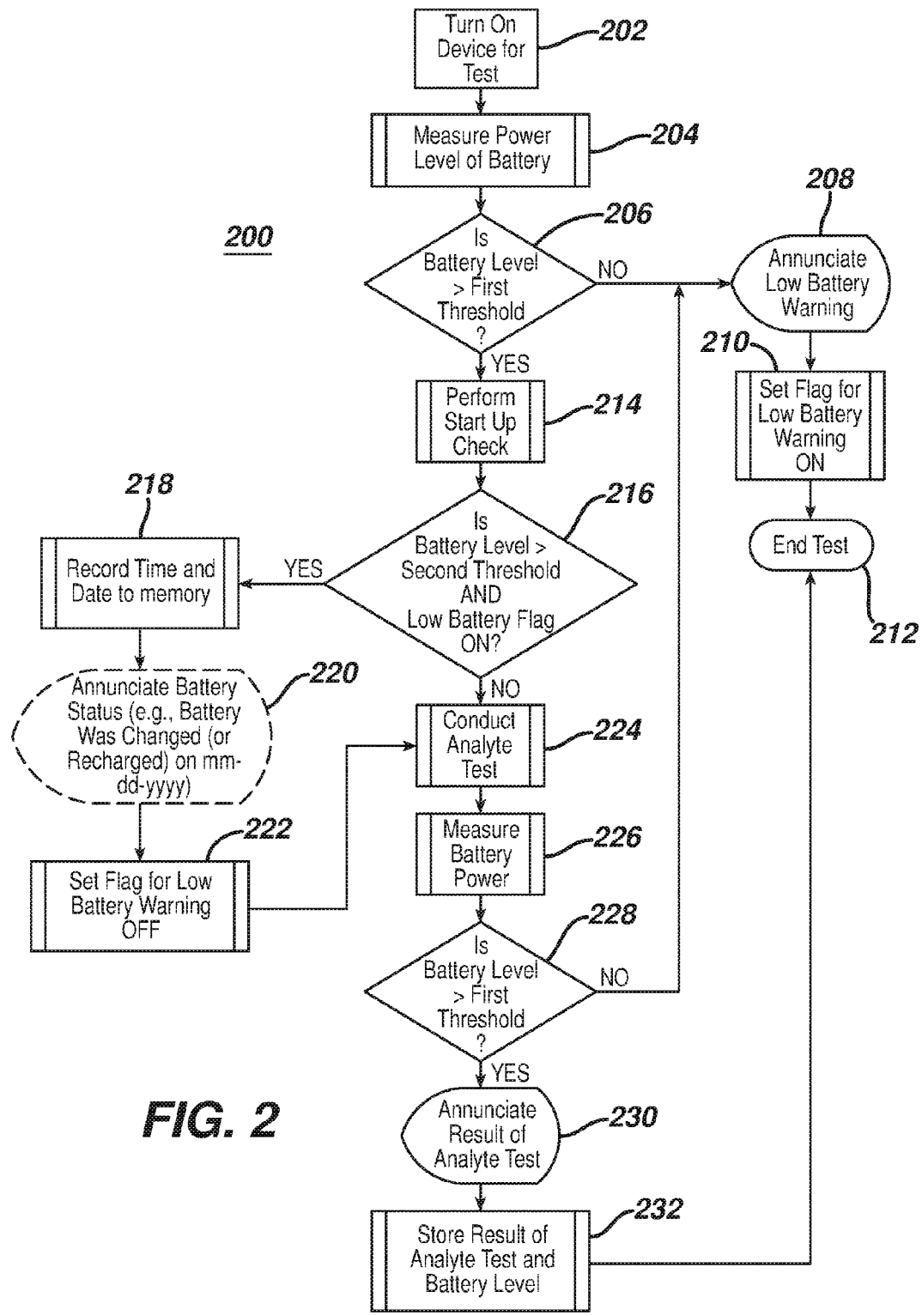
FIG. 2 illustrates a process in which the system determines an actual battery change or a fully charged battery and avoids a false positive due to battery removal and insertion.

In FIG. 2, a process flow 200 for battery status detection is provided. In a typical operation, process 200 starts at step 202 when the device 10 is turned for a measurement test (either manually or automatically). At step 204, the system measures the power level of the battery. At step 206, the logic evaluates as to whether the battery level is greater than a first threshold. If step 206 returns a false or negative (i.e., the batter level is at or lower than the first threshold) then the process moves to step 208 in which a low battery warning is annunciated to the user and a low battery flag is turned on at step 210. Thereafter, the system turns off the device at step 212.

Referring back to step 206, where the process has determined that the battery level is greater than the first threshold, the system moves to step 214 to perform a start-up check process for the system. After the system start up check, a battery status change is detected by way of query 216 in which both the battery level and the low battery flag are evaluated together. Specifically, the logic determines in step 216 whether both the battery level is above a second threshold and the low battery flag is turned on. If step 216 returns a true or affirmative then this means that a new battery has been inserted due to the battery level being greater than the second threshold, which is higher than the first threshold. Because the battery low flag has been set, the inference here is that a fresh new battery has been inserted or in the case of rechargeable battery, the battery was fully recharged. Consequently, the logic moves to step 218 to record the battery condition status (e.g., date, time, voltage level, amperage level, electrostatic events, or any other parameters) in a section of the memory separate from the measurement data. Optionally, the system may annunciate this change to the user in step 220. Thereafter, the low battery flag is turned off. The logic then moves back to step 224 for the processor to proceed with the physiological measurement. At step 226, the system checks the battery level to see if the level is greater than the first threshold. If the check or query at step 228 returns a true or affirmative then the system can proceed to annunciating the result of the measurement test at step 230 and the result, along with the battery level (e.g., voltage or power) and other data are stored in the measurement test record memory. On the other hand, if the check at step 228 returns a false or negative (i.e., the battery level is below the first threshold), the system moves to step 208 to annunciate a low battery warning along with setting the low battery level flag on and terminating the process in step 212 to conserve any battery level that remains. As used herein, the term "annunciated" and variations on its root term indicate that an announcement may be provided via text, audio, visual or a combination of all modes or mediums of communication to a user.

In the embodiments described and illustrated herein, the first threshold can be a voltage level indicative of low power reserve, such as, for example, a voltage as measured against a fixed load over time or amp-hour as measured against a fixed load. Specifically, in the embodiments described herein, the battery supply is two AA ALKALINE-sized batteries which provide nominally about 3 volts. For the low battery warning, the first threshold may be set at an appropriate voltage or amperage, such as about 75-82% of the rated voltage or amperage of the battery, and for this example, at about 2.47 volts to 2.5 volts. For the second threshold of these embodiments, the high battery change level is set at about 96% of the rated voltage or amperage, which for this example is about 2.9 volts. A depletion threshold was also determined at which voltage or amperage the device can no longer provide reliable measurement testing (determined by applicants to be about 72% of the rated voltage or about 2.4 volts for this particular device).

These thresholds can be determined iteratively for a particular sample size of a particular monitoring device. Specifically, medical monitoring devices were used to measure analyte in samples until the batteries for these devices were depleted and the number of times that measurement were reliably obtained was recorded to provide for an indication of when the batteries would reach a state in which applicants considered to be depleted (i.e., a depletion threshold). Applicants then added a safety margin to the depletion threshold (e.g., voltage or amperage) level to provide for the first threshold so that a dead battery screen could be displayed for a required time period. This required time period was defined as the time period to have at least 140-250 reliable analyte measurement tests from the low battery (i.e., at the first threshold) to a depleted battery (i.e., at the depletion threshold). For the second threshold, a particular value (e.g., 2.9 volt when 2 AA ALKALINE batteries were used) was chosen so that any self recovery of the batteries didn't trigger a change threshold, and that if brand new batteries (or fully recharged batteries) were not used a battery change (or full recharged) log would still be generated.

By virtue of the systems and methods described herein, a benefit has been achieved in allowing the portable measurement device to detect or infer when the operational status of a power supply (e.g., change in battery or being fully charged) in the device. As well, the change in battery status can be saved separately from the physiological measurement records, thereby reducing or virtually eliminating lost records of battery status over the life of the medical device.

Furthermore, the various methods described herein can be used to generate software codes using off-the-shelf software development tools such as, for example, Visual Studio 6.0, C or C++ (and its variants), Windows 2000 Server, and SQL Server 2000. The methods, however, may be transformed into other software languages depending on the requirements and the availability of new software languages for coding the methods. Additionally, the various methods described, once transformed into suitable software codes, may be embodied in any computer-readable storage medium that, when executed by a suitable microprocessor or computer, are operable to carry out the steps described in these methods along with any other necessary steps.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of monitoring power in a portable physiological measurement device that has at least a battery coupled to a microprocessor and memory, the method comprising the steps of:
   turning on the device;
   measuring the power level of the battery with the microprocessor;
   determining if the measured power level of the battery is greater than a first threshold;
   if the measured power level is less than or equal to the first threshold then setting an internal flag in the microprocessor for low battery as true, and if the measured power level is greater than the first threshold, then performing a start up checking process of the device;
   after the performing of the startup checking process, evaluating the battery with the microprocessor to determine if both the power level of the battery is greater than a second threshold and the low battery flag is set as true;
   if the evaluating step indicates that both the power level of the battery is greater than the second threshold and the internal low battery flag is set as true, then recording the time and date of the evaluating step to memory as one battery status notice of a plurality of battery status notices without deleting another battery status notice of the plurality of battery status notices, setting the internal flag for low battery as false, and annunciating a status of the battery in the device;
   if the evaluating step indicates that either the power level of the battery is not greater than the second threshold or the internal flag for low battery is set as false, then conducting an analyte measurement;
   measuring the power level of the battery with the microprocessor against the first threshold;
   if the measuring indicates that the power level of the battery is greater than the first threshold, then annunciating a result of the physiological measurement, otherwise ending the measuring step; and
   evaluating the plurality of battery status notices to determine a number of battery change events in the life of the measurement device.

2. The method of claim 1, in which the conducting of the physiological measurement comprises measuring an amount of analyte in a biosensor unit.

3. The method of claim 1, in which the battery includes two Alkaline AA-sized batteries and the first threshold comprises 2.5 volts for the battery.

4. The method of claim 1, in which the first threshold comprises 82% of the rated voltage or amperage of the battery.

5. The method of claim 1, in which the second threshold comprises 96% of the rated voltage or amperage of the battery.

6. The method of claim 3, in which the second threshold comprises 2.9 volts for the battery.

7. The method of claim 1, wherein the performing of the startup checking process further comprises providing a tutorial for operation of the device.

8. The method of claim 1, in which the annunciating step comprises displaying the time and date of the evaluating step to indicate that the battery has been recharged or changed.

9. The method of claim 1, further comprising terminating operation of the method whenever the power level of the battery is below the first threshold.

10. A physiological measurement system comprising:
a biosensor unit that provides physiological data of a user; and
a portable disease management unit comprising:
    a microprocessor in communication with the biosensor unit to receive a plurality of physiological measurements reflective of a health condition of the user, the microprocessor being coupled to a memory and a battery; the microprocessor being configured to:
    set an internal low battery flag as true when a power level of the battery is lower than a first threshold;
    evaluate whether both a power level of the battery is greater than a second threshold and the internal low battery flag is true;
    store in the memory one battery status notice of a plurality of battery status notices without deleting another battery status notice of the plurality of battery status notices, the one battery status notice comprising a time and date as well as the measured power level; and
    store in the memory a battery status change only when an evaluation indicates that both the power level of the battery is greater than a second threshold and the low battery flag is true;
    set the internal low battery flag as false when battery status change is stored in memory;
    annunciate to the user that a status of the battery has changed at the time and date stored in memory; and
    evaluate the plurality of battery status notices to determine a number of battery change events in the life of the management unit.

11. The system of claim 10, in which the microprocessor is configured, upon being turned on, to:
measure a power level of the battery;
determine if the measured power level of the battery is greater than the first threshold;
if the power level is determined to be greater than the first threshold then perform a start up process of the device;
measure analyte with the biosensor unit;
check the power level of the battery against the first threshold; and
annunciate a result of the physiological measurement if the power level is greater than the first threshold and otherwise terminate operation.

12. The system of claim 11, in which the physiological measurement includes measurement of an amount of analyte from a physiological fluid in the biosensor unit in the form of a test strip.

13. The system of claim 11, in which the battery includes two Alkaline AA-sized batteries and the first threshold comprises 2.5 volts for the battery.

14. The system of claim 11, in which the first threshold comprises 82% of the rated voltage or amperage of the battery.

15. The system of claim 11, in which the second threshold comprises 96% of the rated voltage or amperage of the battery.

16. The system of claim 11, in which the second threshold comprises 2.9 volts for the battery.

17. The system of claim 11, in which the annunciation comprises display of the time and date of the evaluation to indicate that the battery has been recharged or changed.

18. A method of monitoring battery power in a portable electronic medical device that has at least a battery coupled to a processor and memory, the method comprising the steps of:
measuring a power level of the battery using a microprocessor of the device;
determining if the measured power level of the battery is greater than a first threshold;
if the measured power level is less than or equal to the first threshold, then setting an internal flag of the microprocessor for low battery as true, otherwise performing at least one other process step for the device;
after the performing of the at least one other process step, evaluating the battery using the microprocessor to determine if both the power level of the battery is greater than a second threshold and the internal low battery flag is set as true;
if the evaluating step indicates that both the power level of the battery is greater than the second threshold and the internal low battery flag is set as true then recording the time and date of the evaluating step to memory as well as the measured power level as one battery status notice of a plurality of battery status notices without deleting another battery status notice of the plurality of battery status notices, and storing a battery status change and setting the internal flag for low battery as false;
annunciating a change in status of the battery in the device; and
evaluating the plurality of battery status notices to determine a number of battery change events in the life of the medical device.

19. The method of claim 18, in which the battery includes two Alkaline AA-sized batteries and the first threshold comprises 2.5 volts for the battery.

20. The method of claim 18, in which the first threshold comprises 82% of the rated voltage or amperage of the battery.

21. The method of claim 18, in which the second threshold comprises 96% of the rated voltage or amperage of the battery.

22. The method of claim 19, in which the second threshold comprises 2.9 volts for the battery.

23. The method of claim 18, wherein the performing step further comprises providing a tutorial for operation of the device.

24. The method of claim 18, in which the annunciating step comprises displaying the time and date of the evaluating step to indicate that the battery has been recharged or changed.

25. The method of claim 18, further comprising terminating operation of the method whenever the power level of the battery is below the first threshold.

* * * * *